United States Patent [19]

Báthory et al.

[11] 3,937,694

[45] Feb. 10, 1976

[54] PROCESS FOR THE RECOVERY OF ZINC BACITRACIN FREE FROM ZINC HYDROXIDE

[75] Inventors: Judit Báthory; Márta Éry née Nagy; Lajos Gerei; Ferenc Lakatos; Mágdolna Stiller née Kisteleki; Tamás Vághy, all of Budapest, Hungary

[73] Assignee: Phylaxia Oltoanyag- es Tapszertermelo Vallalat, Budapest, Hungary

[22] Filed: Apr. 12, 1974

[21] Appl. No.: 460,574

[30] Foreign Application Priority Data
Apr. 16, 1973 Hungary............................... PI 380

[52] U.S. Cl........................................ 260/112.5 R
[51] Int. Cl.² ................. C07C 103/52; C07G 7/00; C08H 1/00
[58] Field of Search................... 260/112.5; 424/177

[56] References Cited
UNITED STATES PATENTS

| 2,457,887 | 1/1949 | Goorley | 260/112.5 |
| 2,582,921 | 1/1952 | Charney | 260/112.5 |
| 2,809,892 | 10/1957 | Chornock | 424/177 |
| 2,834,711 | 5/1958 | Zinn et al. | 260/112.5 |
| 3,025,216 | 3/1962 | Ziffer et al. | 424/177 |
| 3,795,663 | 5/1974 | Miescher | 260/112.5 |

Primary Examiner—Lewis Gotts
Assistant Examiner—Reginald J. Suyat
Attorney, Agent, or Firm—Karl F. Ross; Herbert Dubno

[57] ABSTRACT

A process for the recovery of bacitracin in the form of a zinc complex wherein the pH is raised to precipitate the zinc bacitracin complex. The zinc bacitracin complex is precipitated in the presence of ammonium ion which complexes the excess zinc and maintains it in solution, thereby preventing coprecipitation of zinc hydroxide.

3 Claims, No Drawings

PROCESS FOR THE RECOVERY OF ZINC BACITRACIN FREE FROM ZINC HYDROXIDE

FIELD OF THE INVENTION

The invention relates to an improved process for the recovery of bacitracin from a fermentation liquor of bacitracin or from bacitracin-containing aqueous solutions by complex forming with bivalent metals capable of formation a metal-bacitracin complex.

BACKGROUND OF THE INVENTION

Bacitracin is a water-soluble unstable cyclic polypeptide produced by cultivation of B. subtilis or B. licheniformis on a submerged nutrient medium under aerobic conditions and is particularly effective against gram-positive microorganisms. Bacitracin is widely, nearly exclusively, used for animal feed purposes; this aspect of its use is believed to be more important than its use in human therapy. It exerts an influence on the intestinal flora of the animals. When used as a feed supplement it promotes growth of the young animals and the utilization of the feed. It is the only antibiotic which does not inhibit the functioning of the micro flora of the digestive tract of ruminants even in large doses, but inhibits the reproduction of pathogenic microorganisms. Its use is particularly advantageous since it is not absorbed and cannot be detected in the animal products (meat, milk etc.). Because it is not used for therapeutic purposes the problem of developed resistance is negligible.

Bacitracin produced by fermentation is very unstable in a pure stage it is very complicated to prepare bacitracin from the available dilute solution formulations. Several methods are known for the preparation of products of high bacitracin content.

According to the methods described for example in U.S. Pat. Nos. 2,582,921; 2,457,887 and 2,739,063 bacitracin is precipitated from dilute solutions on inorganic carriers. The common feature of these methods is the low yield and the instability of the product.

In accordance with other known methods bacitracin is recovered by extraction with organic solvents as described in U.S. Pat. Nos. 2,498,165 and 2,609,324. These methods involve the disadvantage that large amounts of solvent are required, the solvents must be regenerated, the yield is low and the extraction is not selective.

According to further known methods (U.S. Pat. Nos. 2,776,240 and 2,915,432) bacitracin is recovered by ion-exchange sorption. It is a deficiency of these methods however, that the yield is low and the technology is complicated.

The isolation of bacitracin in the form of complexes is described in U.S. Pat. Nos. 2,556,375, 2,774,712 and 3,035,919, Czechoslovak Pat. No. 119,180 and Hungarian Pat. No. 157,983. These methods are less complicated than those mentioned before and the bacitracin content of the product is higher but the precipitating agents are expensive and some of them have analgetic properties.

Bacitracin can be isolated in the form of a complex by means of Zn, Mn, Ni or Co salts (U.S. Pat. Nos. 2,809,892; 3,025,216; 2,903,357; 2,985,533; 2,985,534 and 3,021,217). In accordance with U.S. Pat. No. 2,809,892 a water-soluble zinc salt is added to the acidified fermentation liquor of bacitracin, zinc bacitracin is precipitated by raising the pH of the mixture, the zinc bacitracin complex is separated and the separated complex is dried. The metal complexes obtained are stable but the bacitracin content does not exceed 4 to 8 % owing to the co-precipitation of the metal hydroxides and complicated methods, e.g. ion exchange sorption are needed to purify the product (U.S. Pat. No. 2,834,711).

OBJECT OF THE INVENTION

The object of the present invention is to provide an economical process for recovering bacitracin from aqueous solutions, particularly from fermentation liquors in high yield in the form of a stable complex of high bacitracin content.

DESCRIPTION OF THE INVENTION

The invention is based on the recognition that the yield and the bacitracin content is increased by the excess of the bivalent metal ions capable of complex forming, particularly that of the zinc ions used for forming the bacitracin complex provided that the metal hydroxide formed remains in solution.

It has been found that when the bacitacin-complex formation is carried out in the presence of $NH_4^+$-ions, a metal-bacitracin complex having a bacitracin-content of 30–40 % is obtained.

In accordance with the present invention the process for the recovery of bacitracin from fermentation liquors or from bacitracin-containing aqueous solutions is carried out by adding a water-soluble salt of a bivalent metal capable of bacitracin-complex formation, preferably a zinc salt, and an ammonium salt to the acidified and filtered fermentation liquor or to the acidified aqueous solution of bacitracin and raising the pH to precipitate the metal-bacitracin complex, separating the precipitated complex from the mother liquor and drying the product (i.e. the metal-bacitracin complex).

According to a preferred embodiment the ammonium salt is added to the fermentation liquor in two steps, that is a part of the $NH_4^+$-ions is added to the fermentation liquor prior to filtering thereof at a pH of 2.5 – 3. In this way the fermentation liquor can be easily filtered as a considerable part of the accompanying other proteins present in the fermentation liquor is precipitated by the ammonium salt. The remaining $NH_4^+$ is added to the filtered solution to complex with the metal which otherwise would precipitate as the hydroxide.

The process according to the invention represents considerable technical progress in relation to the known methods since it permits the recovery of bacitracin with a yield with 70–90 % and a composition with a bacitracin content of 30–40 %; the bacitracin complex is stable for 1-2 years, there is no need for expensive reactants and the reactants need not be regenerated. The product obtained is free from the metal hydroxides.

SPECIFIC EXAMPLES

The following examples illustrate the specific embodiments of the invention. The bacitracin content of the product was determined in microbiological way using Micrococcus flavus ATCC 10 240 as the test organism (Kavanagh: Analytical microbiology 261-264. (1963) Academic Press, New York).

EXAMPLE 1

To a fermentation liquor containing 312 units/ml of bacitracin and having a pH of 7.8, 10 % by weight of ammonium sulfate (calculated on the weight of the fermentation liquor) is added. The pH is adjusted with conc. sulfuric acid to pH 3 and the fermentation liquor is filtered. To 500 ml of the filtrate, 10 % by weight of ammonium sulfate and 2.5 g of $ZnSO_4 \cdot 7 H_2O$ are added. The pH is adjusted with ammonium hydroxide to 7.5, the solution is stirred, filtered and the filtered precipitate is dried in vacuo at 40°C. Thus 6.3 g of a product containing 37.2 % of bacitracin are obtained, which represents a yield of 75.0 %.

EXAMPLE 2

To 500 ml of a fermentation liquor containing 320 units/ml of bacitracin and having a pH of 3.2, 50 g of ammonium sulfate and 5 g of zinc sulfate are added. The pH is adjusted with a sodium hydroxide solution to 7.2 and the mixture is filtered. The precipitate is dried in vacuo at 40°C. Thus 5.6 g of a product containing 40 % of bacitracin are obtained, which represents a yield of 70.4 %.

EXAMPLE 3

The pH of an aqueous solution containing 285 units/ml of bacitracin is adjusted with sulfuric acid to 2.8 and 10 % by weight of ammonium sulfate (calculated on the weight of the solution) are added. To 1500 ml of the solution 150 g of ammonium sulfate and 60 g of $ZnSO_4 \cdot 7 H_2O$ are added, the pH is adjusted with ammonium hydroxide to 8 and the solution is stirred. Then the precipitate is filtered and dried in vacuo at 40°C. Thus 30.8 g of a product containing 25 % of bacitracin are obtained, which represents a yield of 90.3 %.

EXAMPLE 4

To 2000 ml of a filtered fermentation liquor containing 330 units/ml of bacitracin and having a pH of 3, 200 g of ammonium sulfate and a water-soluble zinc salt are added in an amount corresponding to 9.12 g of zinc-ions. The pH of the solution is adjusted with ammonium hydroxide solution to 7.5, the precipitate is filtered and dried in vacuo at 35°C. Thus 28.3 g of a product containing 38.5 % of bacitracin are obtained, which represents a yield of 82.5 %.

EXAMPLE 5

To 1000 ml of a filtered fermentation liquor containing 292 units/ml of bacitracin and having a pH of 3.0, 10 g of ammonium sulfate and a water-soluble zinc salt are added in an amount corresponding to 6.8 g of zinc-ions. The pH is adjusted with ammonium hydroxide solution to 8.3 and the mixture is stirred. Then the product is filtered and dried in vacuo at 30°C. Thus 15.7 g of a product containing 30 % of bacitracin are obtained, which represents a yield of 80.5 %.

The zinc-content of the product obtained by the process of the invention only after the digestion of the proteins carried out by destruction can be determined.

What we claim is:

1. A process for the recovery of bacitracin from a solution containing same which comprises the step of raising the pH of said solution in the presence of zinc ion from a soluble zinc source added to the solution and in the presence of ammonium ion to precipitate the bacitracin in the form of a zinc bacitracin complex while maintaining zinc which does not form said zinc bacitracin complex in solution; removing the zinc bacitracin complex precipitated from said solution; and drying the zinc bacitracin complex precipitate.

2. The process defined in claim 1 wherein, prior to raising the pH of the solution, the solution is acidified to a pH 2.5 to 3, ammonium ion is added to the acidified solution to precipitate protein therefrom, and the precipitated protein is removed from the solution, the zinc salt being added only after the precipitated protein has been removed.

3. The process defined in claim 1 wherein the solution from which the zinc bacitracin complex is precipitated is a fermentation liquor.

\* \* \* \* \*